United States Patent [19]

Yu

[11] Patent Number: 5,582,869
[45] Date of Patent: Dec. 10, 1996

[54] LOW LEACHING COMPOSITIONS FOR WOOD

[75] Inventor: Bing Yu, Horsham, Pa.

[73] Assignee: Rohm and Haas Company, Philadelphia, Pa.

[21] Appl. No.: 470,192

[22] Filed: Jun. 6, 1995

Related U.S. Application Data

[62] Division of Ser. No. 255,503, Jun. 8, 1994, Pat. No. 5,536,305.

[51] Int. Cl.$^6$ .............................. B05D 7/06; A01N 43/74
[52] U.S. Cl. .................. 427/297; 106/15.05; 106/18.32; 106/18.33; 106/18.35; 427/397
[58] Field of Search ............... 106/15.05, 18.32, 106/18.33, 18.34, 18.35; 427/297, 397; 424/405; 514/372

[56] References Cited

U.S. PATENT DOCUMENTS

| | | | |
|---|---|---|---|
| 3,761,488 | 9/1973 | Lewis et al. | 106/18.32 |
| 4,265,899 | 5/1981 | Lewis et al. | 514/372 |
| 4,279,762 | 7/1981 | Lewis et al. | 252/47.5 |
| 4,325,201 | 4/1982 | Lewis et al. | 514/372 |
| 4,507,152 | 3/1985 | Collins et al. | 106/18.35 |
| 4,783,221 | 11/1988 | Grove | 106/18.22 |
| 4,954,338 | 9/1990 | Mattox | 424/78 |
| 5,200,188 | 4/1993 | Mattox | 424/405 |
| 5,223,524 | 6/1993 | Valcke | 514/383 |
| 5,536,305 | 7/1996 | Yu | 514/372 |

FOREIGN PATENT DOCUMENTS 148526  7/1985  European Pat. Off. .

Primary Examiner—Anthony Green

[57] ABSTRACT

The invention concerns a method of protecting wood comprising the steps of (a) treating said wood with a composition consisting essentially of (i) 4,5-dichloro-2-n-octyl-3-isothiazolone and optionally one or more other preservative compounds; (ii) a surfactant system consisting of at least one surfactant selected from the group consisting of sulfated anionics, sulfonated anionics, sulfosuccinated anionics, quaternary ammonium cationics, and amphoterics; and (iii) at least one non-polar organic solvent and (b) allowing said solvent to evaporate from said wood.

4 Claims, No Drawings

LOW LEACHING COMPOSITIONS FOR WOOD

This is a divisional of application Ser. No. 08/255,503, filed Jun. 8, 1994, now U.S. Pat. No. 5,536,305.

BACKGROUND OF THE INVENTION

1. Field of the Invention

This invention relates to wood preservative compositions and methods.

2. Description of the Prior Art

Wood requires treatment with microbicides to prevent staining and decay by microorganisms. By wood is meant lumber, timber, posts, wood coverings, wicker, millwork, joinery, wood products such as plywood, fiberboard, chipboard, waferboard, particleboard, and other wood products used in construction.

Freshly milled timber and wood for millwork/joinery are usually treated with preservatives by dipping and double vacuum treatments. Wood for use in ground and many above ground applications are usually treated with a preservative by pressure treatment. Preservatives can also be applied by brushing, spraying, soaking, and similar treatment methods.

The most important current commercial wood preservative, especially for pressure treating applications, is CCA (chromated copper arsenate). After treatment with CCA, there is a waiting period to allow for fixation of the metals into the wood before it can be used. During this fixation period, ground contamination from chromium, copper, and arsenic can occur if proper containment procedures are not followed. While CCA is very effective for wood preservation, disposal of unwanted CCA treated wood is becoming a problem. In some places, unwanted CCA treated wood is considered hazardous waste requiring special disposal procedures. There is also concern about leaching of copper, chromium and arsenic from CCA treated wood during its use.

As an alternative to CCA, certain water insoluble organic preservative compounds have been proposed. Such organic compounds do not require a fixation period and unwanted treated wood should not be considered hazardous waste. U.S. Pat. No. 4,954,338 teaches microemulsions of isothiazolone wood treatment compounds which require the use of certain surfactants. European Patent Application 0148526 discloses a water-dilutable formulation for the azole class of preservatives with preferred surfactants. Upon exposure to water, the organic wood preservative compounds applied by prior methods and compositions are all believed to suffer from the problem that the preservative leaches from the wood at too great of a rate.

SUMMARY OF THE INVENTION

The present invention provides compositions in both concentrate and water-diluted forms, comprising (a) at least one organic, water insoluble wood preservative compound; (b) a surfactant system consisting of one or more surfactants selected from the group consisting of sulfated anionics; sulfonated anionics; sulfosuccinated anionics; quaternary ammonium cationics; and amphoterics; and (c) optional non-polar organic solvent, such compositions being useful in a method of wood treatment which results in treated wood having improved properties with regard to lower rates of leaching of the organic preservative compound than having been achieved with prior water-based compositions and methods.

DETAILED DESCRIPTION OF THE INVENTION AND THE PREFERRED EMBODIMENTS

One or more organic, water insoluble wood preservative compounds, preferably less than 1000 ppm soluble in water at room temperature, can be used. Suitable wood preservative compounds are 3-isothiazolones such as 2-n-octyl-3-isothiazolone, and 4,5-dichloro-2-n-octyl-3-isothiazolone; propiconazole; tebuconazole; fenbuconazole; myclobutanil; azaconazole; iodopropargyl butyl carbamate; 2-thiocyanomethyl(thio)benzothiazole; chlorpyrifos; chlorothalonil; permethrin; dichlofluanid; cyfluthrin; cypermethrin; copper-8-quinolinolate; s-fenvalerate; bifenthrin; o-phenylphenol; dithiocarbamate compounds; copper naphthenate; zinc naphthenate; zinc acypetacs; tributyltin oxide; pentachlorophenol; quaternary compounds; and the like.

One or more non-polar organic solvent can be used in the concentrates, said solvent being optional when all of the wood preservative compounds have a melting point below or equal to 25° C., but such solvent being required when wood preservative compound having a melting point above 25° C. is present. Suitable organic solvents include benzyl alcohol, benzyl acetate, pine oil, phenethyl alcohol, xylene, phenoxyethanol, butyl phthalate, 2,2,4-trimethyl-1,3-pentanediol monoisobutyrate, mixtures of alkylbenzenes, P9 oil, long chain alkyl acrylate esters, and mineral spirits. Such organic solvent should be capable of dissolving at least 5% by weight of the wood preservative compound at 25° C.

The wood preservative compound is preferably 4,5-dichloro-2-n-octyl-3-isothiazolone or combinations of that compound with one of the aforementioned other compounds, especially with propiconazole. The compound(s) is preferably supplied in the form of a "concentrate" composition which, in addition to the compound(s), comprises surfactant, optional solvent, and optional adjuvants, and is suitable for dilution with water to form a microemulsion or an emulsion. The microemulsion or emulsion is the composition which is applied to the wood. When water is added to the concentrate composition, the resultant weight ratio of water to concentrate composition is 0.1:99.9 to 99.9:0.1. The microemulsion or emulsion can also prepared directly, i.e., without first preparing the concentrate, simply by combining the wood preservative compound, surfactant system, any adjuvants, and the appropriate mount of water, at the same time.

When the compositions are in the form of microemulsion, they remain microemulsion at all levels of water dilution. The microemulsion compositions remain thermodynamically stable and dear, opalescent, or only slightly cloudy at all levels of water dilution up to 99.9%.

Suitable adjuvants including antifoam agents, antifreeze agents, wetting agents, thickeners, and the like can be added to either the concentrates or the emulsions or microemulsions.

When a wood treatment compound having a melting point above 25° C. is used, concentrate compositions can be prepared by dissolving solid wood preservative compound in an organic solvent to form the oil phase. The surfactants can then be added to the oil phase, either individually or in combination if more than one surfactant is used. If the surfactant system is in paste or solid form, it is preferred to premelt the surfactant system prior to mixing it with the oil phase. The resulting mixture is gently stirred or agitated to give a concentrate. Alternatively, if the solid wood preservative compound is heat stable, all the components may be added together in a single vessel and the vessel heated slightly to form the microemulsion concentrate. The latter method has the advantage that it is a one-step addition. When the wood preservative compound is a liquid at 25° C., organic solvent is not necessary, and such compound may be used itself as the oil phase without the addition of an organic solvent. It is further preferred that the oil phase be formed first and the surfactant system be added to it.

The surfactant system consists only of one or more surfactant selected from the group consisting of sulfated anionics; sulfonated anionics; sulfosuccinated anionics; quaternary ammonium cationics; and amphoterics.

Preferred sulfated or sulfonated anionic surfactants have about 3–17% sulfation or sulfonation, and are selected from the group consisting of sulfated and/or sulfonated castor oil, sulfated and/or sulfonated ethoxylated alkylphenols, sulfated and/or sulfonated ethoxylated fatty alcohols, sulfated and/or sulfonated fatty adds, and sulfated alkanolamides, and sulfosuccinated anionic surfactants selected from the group consisting of monoalkylsulfosuccinate, dialkylsulfosuccinate, and fatty alcohol ether sulfosuccinate monoester or diester.

Preferred anionic surfactants include amyl ester of sulfonated oleic add, sodium salt; sulfated castor oil (6–7% sulfation); disodium ethoxylated nonylphenol half ester of sulfosuccinate acid; sulfated fatty add; and dioctyl ester of sodium sulfosuccinic add.

Preferred quaternary ammonium cationic surfactants are N-alkyl (50% $C_{14}$, 40% $C_{12}$ to 10% $C_{16}$) dimethyl benzyl ammonium chloride; polypropylene diethyl ammonium phosphate; dodecyl methylpolyoxyethylene ammonium chloride; bis (hydrogenated tallow) dimethyl ammonium chloride; trimethyl coco quaternary ammonium chloride; dimethyl didecyl ammonium chloride; methyl bis(2-hydroxyethyl)coco-ammonium chloride; and N,N-didecyl-N-methyl-poly(oxyethyl) ammonium propionate.

Preferred amphoteric surfactants are N-alkyl aminopropionates, N-alkyl iminopropionates, N-alkyl betaines, N-alkyl glycinate, carboxy glycinate, alkyl imidazolines, alkyl polyamino carboxylates, polyamphocarboxy glycinates, amine oxides, cocoamphocarboxypropionate, cocamidopropyl betaine, coco aminopropyl sulfo betaine; and cocamphocarboxy glycinate.

Preferred surfactant systems are those where only one anionic is used; two anionics are used; an anionic and an amphoteric are used; two quaternary ammonium cationics are used; a quaternary ammonium cationic and an amphoteric are used; or two quaternary ammonium cationics and an amphoteric are used. Two especially preferred surfactant systems are sulfonated castor oil and dioctyl ester of sodium sulfosuccinic acid.

It has been discovered that the surfactant system is critical to the obtention of the low leaching quality of the wood preservative system.

The preferred concentrate compositions comprise about 0.1 to 30 parts by weight wood preservative compound, 0.1 to 99.9 parts by weight surfactant, and 0 to 99.8 parts by weight solvent, based on 100 parts total of wood preservative compound, surfactant system, and solvent plus up to about 10 parts of adjuvants. More preferred concentrate compositions comprise about 5 to 25 parts by weight wood preservative compound, 20 to 80 parts by weight surfactant, and 25 to 75 parts by weight solvent, based on 100 parts total of wood preservative compound, surfactant system, and solvent. The most preferred concentrate compositions comprise about 15 to 25 parts by weight wood preservative compound, 40 to 70 parts by weight surfactant, and 25 to 40 parts by weight solvent, based on 100 parts total of wood preservative compound, surfactant system, and solvent. The ratio of wood preservative compound to surfactant is from about 1 to 20 to about 1 to 1, preferably from about 1 to 8 to about 1 to 2, and most preferably from about 1 to 4 to about 1 to 2. The ratio of wood preservative compound to solvent when one is used is from about 1 to 50 to about 20 to 1, preferably from about 1 to 4 to about 4 to 1, and most preferably from about 1 to 3 to about 1 to 1. The preferred concentrate compositions are dilutable with water to form compositions which maintain their microemulsion character at all levels of water dilution.

The compositions are applied to wood by pressure treatment, vacuum treatment, dipping, brushing, spraying, or soaking, for example. After treatment, the water and any solvent are removed by any method, for example, by evaporation. The compositions of the invention are especially suitable for use in pressure treating wood, particularly softwood, for use in above-ground and in-ground contact applications. These compositions can also be used for preserving freshly sawn timber.

Preferrably, the wood is pressure treated or vacuum treated so as to achieve a higher level of impregnation, and then the solvent is allowed to evaporate, leaving wood preservative compound which protects the wood from fungal growth. The advantage of the present invention is that the wood preservative compound is resistant to leaching when treated wood is exposed to water.

EXAMPLE 1

Formulations

Table 1 shows the composition of the microemulsion concentrates used in the following examples. These samples were prepared by dissolving the wood preservative compound ("AI") in an organic solvent to yield an oil phase, and adding the desired surfactant(s) to yield a microemulsion concentrate (MEC).

The abbreviations used in the following Tables and Examples are as follows:

Wood Preservative Compound
AI 1=4,5-dichloro-2-n-octyl-3-isothiazolone
AI 2=propiconazole
AI 3=CCA (chromated copper arsenic)
Solvent #

---

1 Benxzyl alcohol
2 P9 oil (petroleum distillate with 90% volume distilling point of 307° C.)
3 Mineral spirits
4 Aromatic ® 150 (a mixture of alkylbenzenes)
5 2,2,4-Trimethyl-1,3-pentanediol monoisobutyrate
6 Benzyl acetate
7 Isodecyl methacrylate
8 Water

---

Surfactants
  Sulfated, Sulfonated, and Sulfosuccinated Anionics

---

| | |
|---|---|
| A | 70% Amyl ester sulfonated oleic acid, sodium salt |
| B | 70% Sulfated castor oil (6–7% sulfation) |
| C | 34% Disodium ethoxylated nonylphenol half ester of sulfosuccinate acid |
| D | 70% Sulfated fatty acid |
| E | 100% Dioctyl ester of sodium sulfosuccinic acid |

Quaternary Ammonium Cationics

| | | |
|---|---|---|
| F | 75% | Methyl bis(2-hydroxyethyl)coco-ammonium chloride |
| G | 80% | N-alkyl(50% C14, 40% C12, and 10% C16) dimethyl benzyl ammonium chloride |
| H | 100% | Propylene diethyl ammonium phosphate |

Betaines and Amphoterics

| | | |
|---|---|---|
| I | 39% | Cocoamphocarboxypropionate |
| J | 30% | Cocamidopropyl betaine |
| K | 35 to 45% | Coco aminopropyl sulfo betaine |
| L | 50% | Cocamphocarboxy glycinate |

Others (Comparative).

| | | |
|---|---|---|
| M | 100% | Ethoxylated castor oil (EO = 30) |
| N | 85% | Fatty alcohol ether carboxylic acid |
| O | 100% | Octylphenoxypoly(ethyleneoxy)ethanol (EO = 9) |
| P | 100% | Free acid of a complex aliphatic phosphate mono- and di-esters |

The formulations of the test solutions used in the following Examples are described in Table 1.

The controls used in the following Examples were prepared by dissolving an appropriate amount of AI1 in a solvent. The compositions of the controls are as follows:

| Sample # | AI (ppm) | Solvent |
|---|---|---|
| C1 | 1 (3400–3500) | 2 |
| C2 | 1 (3400–3590) | 3 |

EXAMPLE 2

Leaching Studies (AWPA Standard M11-87)

Wood blocks were pressure treated with test solutions of the invention. These pressure treated blocks were then evaluated for the leaching of AI 1.

The test blocks used were 19 mm cubes of southern yellow pine which had been conditioned to approximately 10% moisture content. All blocks were within a weight range of ±10% of an average of ten blocks to ensure comparable densities of the blocks. The blocks were weighed, and sets of 12 or 18 blocks were placed in plastic beakers. Layers of blocks were separated by a piece of polypropylene plastic grid. The blocks were weighed down with a stainless steel weight.

TABLE 1

| | % AI 1 | % AI 2 | Solvent (%) | Surfactant 1 (%) | Surfactant 2 (%) |
|---|---|---|---|---|---|
| Sample | | | | | |
| 1 | 9.0 | 0 | 1 (21.0) | A (35.0) | I (35.0) |
| 2 | 9.0 | 0 | 1 (21.0) | B (70.0) | — |
| 3 | 9.0 | 0 | 1 (21.0) | F (70.0) | — |
| 4 | 9.0 | 0 | 1 (21.0) | C (70.0) | — |
| 5 | 9.0 | 0 | 1 (21.0) | D (70.0) | — |
| 6 | 9.0 | 0 | 1 (21.0) | A (70.0) | — |
| 7 | 9.0 | 0 | 1 (21.0) | J (35.0) | B (35.0) |
| 8 | 5.0 | 5.0 | 1 (21.0) | A (55.3) | I (23.7) |
| 9 | 25.0 | 0 | 2 (25.0) | B (35.0) | E (15.0) |
| 10 | 25.0 | 0 | 4 (25.0) | B (35.0) | E (15.0) |
| 11 | 20.0 | 0 | 5 (20.0) | B (42.0) | E (18.0) |
| 12 | 18.7 | 6.3 | 2 (25.0) | B (35.0) | E (15.0) |
| 13 | 12.5 | 12.5 | 2 (25.0) | B (35.0) | E (15.0) |
| 14 | 6.3 | 18.7 | 2 (25.0) | B (35.0) | E (15.0) |
| 15 | 25.0 | 0 | 2 (25.0) | B (30.0) | J (20.0) |
| 16 | 20.0 | 0 | 2 (20.0) | A (48.0) | K (24.0) |
| 17 | 20.0 | 0 | 2 (20.0) | G (18.0) | H (42.0) |
| 18 | 15.0 | 0 | 2 (15.0) | G/H (3/7) (35.0) | L (35.0) |
| 19 | 25.0 | 0 | 4 (25.0) | B (35.0) | E (15.0) |
| 20 | 16.0 | 0 | 1 (24.0) | B (36.0) | E (24.0) |
| 21 | 16.0 | 0 | 5 (24.0) | B (30.0) | E (30.0) |
| 22 | 20.0 | 0 | 6 (30.0) | B (35.0) | E (15.0) |
| 23 | 25.0 | 0 | 7 (25.0) | B (35.0) | E (15.0) |
| Comparative | | | | | |
| A | 9.0 | 0 | 1 (21.0) | M (70) | — |
| B | 9.0 | 0 | 1 (21.0) | O (70) | — |
| C | 9.0 | 0 | 1 (21.0) | P (70) | — |
| D | 9.0 | 0 | 1 (21.0) | N (70) | — |

One comparative sample was not a microemusion concentrate. Sample E is the current state of the art in wood preservation, "CCA-C." This sample contains only CCA (AI 3) in water, no surfactants.

| Sample # | AI (ppm) | Solvent |
|---|---|---|
| E | 3 (12900–13300) | 8 |

Test solutions were prepared by diluting the MECs of Example 1 (Samples 1–8) with water to a final concentration of 3400–3500 ppm of total wood preservative compound to yield a microemulsion. The test solutions were mixed on a magnetic stirrer, poured over the test blocks, the beakers covered with aluminum foil placed in a treating cylinder. The control solutions were used as is, without further dilution.

Treatment of the test blocks was carried out by a 30 minute exposure to a vacuum of 25 in. Hg, followed by pressure at 100 psi for 60 minutes. The beakers were removed from the testing cylinder and allowed to stand for 30 minutes to allow for kick-back. The test solution was then poured off. Excess test solution was removed from the blocks by patting the blocks dry with an absorbant towel. The blocks were reweighed, placed on racks in a fume hood at room temperature for 2 days, and then placed in a conditioning room for 21 days.

After conditioning, the blocks were again placed in plastic beakers, weighed down, and covered with 300 ml of distilled water. The beakers were then placed in the treating cylinder and exposed to a vacuum of 25 in. Hg for 30 minutes. The distilled water was removed and replaced after 0.25, 2, 4, 6, 10, and 14 days. Aliquots of each distilled water sample (leachate) were analyzed for the respective wood preservative compound.

The leaching data are reported in Table 2. These data are cumulative totals for the 14 day leaching period. A cumulative percentage of 5.0% or less of wood preservative compound leaching at 14 days is considered passing.

TABLE 2

Cumulative Percentage of 4,5-Dichloro-2-n-octyl-3-isothiazolone Leached from Pressure Treated Wood

| | Days | | | | | |
|---|---|---|---|---|---|---|
| | 0.25 | 2 | 4 | 6 | 10 | 14 |
| Sample # | | | | | | |
| 1 | 1.3 | 2.4 | 3.1 | 3.9 | 4.5 | 5.0 |
| 2 | 0.4 | 0.8 | 1.1 | 1.3 | 1.8 | 2.2 |
| 3 | 1.7 | 2.1 | 2.3 | 2.5 | 2.9 | 3.1 |
| 4 | 1.1 | 1.7 | 1.8 | 2.0 | 2.2 | 2.3 |
| 5 | 0.5 | 1.0 | 1.2 | 1.6 | 2.0 | 2.4 |
| 6 | 1.3 | 2.5 | 2.8 | 3.2 | 3.9 | 4.5 |
| 7 | 1.0 | 1.5 | 1.7 | 2.1 | 2.6 | 3.1 |
| 8 | 0.5 | 1.0 | 1.2 | 1.4 | 1.6 | 1.9 |
| Controls | | | | | | |
| C1 | 0.1 | 0.2 | 0.2 | 0.3 | 0.4 | 0.5 |
| C2 | 0.6 | 1.5 | 2.0 | 2.9 | 3.6 | 4.4 |

From the data in Table 2, it can be seen that the microemulsions of the invention have same low leaching behavior as that of the wood preservative compound in solvent alone.

EXAMPLE 3

Comparative

The percentage of 4,5-dichloro-2-n-octyl-3-isothiazolone leached from wood blocks treated with compositions of the invention was compared to that from wood blocks treated with other compositions.

Test solutions of samples 1 and 2, and comparative samples A, B, C, and D were prepared as described in Example 1. Wood blocks were pressure treated with these test solutions as described in Example 1. The leaching data are reported in Table 3. These data are cumulative totals for the 14 day leaching period. A cumulative percentage of 5.0% or less of wood preservative compound leaching at 14 days is considered passing.

TABLE 3

Cumulative Percentage of 4,5-Dichloro-2-n-octyl-3-isothiazolone Leached from Pressure Treated Wood

| | Days | | | | | |
|---|---|---|---|---|---|---|
| | 0.25 | 2 | 4 | 6 | 10 | 14 |
| Sample # | | | | | | |
| 1 | 1.3 | 2.4 | 3.1 | 3.9 | 4.5 | 5.0 |
| 2 | 0.4 | 0.8 | 1.1 | 1.3 | 1.8 | 2.2 |
| Comparative | | | | | | |
| A | 6.7 | 14.8 | 18.2 | 20.2 | 21.3 | 22.0 |
| B | 5.9 | 13.5 | 17.6 | 19.7 | 20.9 | 21.6 |
| C | 3.5 | 6.4 | 7.2 | 7.7 | 8.1 | 8.4 |
| D | 2.4 | 6.4 | 7.1 | 7.9 | 8.5 | 9.0 |
| Controls | | | | | | |
| C1 | 0.1 | 0.2 | 0.2 | 0.3 | 0.4 | 0.5 |
| C2 | 0.6 | 1.5 | 2.0 | 2.9 | 3.6 | 4.4 |

EXAMPLE 4

Comparative

The percentage of wood preservative compound leached from wood blocks treated with compositions of fire invention was compared to that from wood blocks treated win CCA, which is current commercial art.

Test solutions of samples 2 and E were prepared as described in Example 1. Wood blocks were pressure treated with these test solutions as described in Example 1. The leaching data are reported in Table 4. These data are cumulative totals for the 14 day leaching period. The percentage wood preservative compound leached from CCA is the total percentages of all three wood preservative compounds; copper, chrome and arsenic.

TABLE 4

Cumulative Percentage of Wood Preservative Compound Leached from Pressure Treated Wood

| | Days | | | | | |
|---|---|---|---|---|---|---|
| | 0.25 | 2 | 4 | 6 | 10 | 14 |
| Sample #2 | 0.4 | 0.8 | 1.1 | 1.3 | 1.8 | 2.2 |
| Comparative E | 3.7 | 10.1 | 12.9 | 16.3 | 17.8 | 18.8 |

From these data it can be seen that the compositions of the invention have surprisingly much lower leaching of the wood preservative compound versus the current commercial art.

EXAMPLE 5

Water Dilutability

The water dilutability of the MEC's of Example 1 was determined by adding varying amounts of deionized water and evaluating clarity using a rating scale of 0–5. Sufficient water was added to the samples to form dilutions containing from 10 to 95% water by weight. The rating scale is defined as follows:

0=perfectly dear;
1=dear, very slight opalescence;
2=opalescent;
3=opalescent;
4=cloudy (macroemulsion); and 5=phase separation.

A rating of 3 or lower is considered passing, i.e. the sample remained a microemulsion upon dilution. The results are shown in Table 5.

TABLE 5

Water Dilutability of Microemulsion Samples

| Sample | Water by Weight | | | | | | | | | | |
|---|---|---|---|---|---|---|---|---|---|---|---|
| | 0 | 10 | 20 | 30 | 40 | 50 | 60 | 70 | 80 | 90 | 95 |
| 1 | 0 | 1 | 1 | 2 | 1 | 0 | 0 | 0 | 0 | 0 | 0 |
| 2 | 0 | 0 | 0 | 0 | 0 | 0 | 0 | 0 | 0 | 0 | 0 |
| 3 | 0 | 0 | 0 | 0 | 0 | 0 | 0 | 0 | 0 | 0 | 0 |
| 6 | 3 | 3 | 2 | 2 | 2 | 1 | 1 | 0 | 0 | 0 | 0 |
| 7 | 0 | 0 | 0 | 0 | 0 | 0 | 0 | 0 | 0 | 0 | 0 |
| 9 | 0 | 0 | 0 | 0 | 0 | 1 | 0 | 1 | 1 | 0 | 0 |
| 10 | 0 | 0 | 0 | 0 | 0 | 2 | 2 | 3 | 1 | 0 | 0 |
| 11 | 0 | 1 | 2 | 3 | 0 | 0 | 0 | 0 | 1 | 1 | 1 |
| 12 | 0 | 0 | 0 | 0 | 0 | 2 | 3 | 3 | 2 | 1 | 0 |
| 13 | 0 | 0 | 0 | 0 | 0 | 2 | 3 | 3 | 2 | 1 | 0 |
| 14 | 0 | 0 | 0 | 0 | 0 | 2 | 3 | 3 | 2 | 1 | 0 |
| 15 | 0 | 0 | 0 | 0 | 0 | 0 | 2 | 2 | 2 | 2 | 2 |
| 16 | 0 | 0 | 0 | 0 | 0 | 0 | 0 | 0 | 0 | 0 | 0 |
| 17 | 0 | 0 | 0 | 0 | 0 | 0 | 0 | 0 | 0 | 0 | 0 |
| 18 | 1 | 1 | 1 | 1 | 1 | 1 | 1 | 3 | 3 | 0 | 0 |
| 19 | 0 | 0 | 0 | 0 | 3 | 3 | 1 | 3 | 3 | 1 | 1 |
| 20 | 1 | 1 | 1 | 1 | 1 | 1 | 1 | 1 | 0 | 0 | 0 |
| 21 | 0 | 2 | 2 | 3 | 3 | 3 | 3 | 3 | 2 | 0 | 0 |
| 22 | 0 | 0 | 0 | 0 | 0 | 0 | 0 | 0 | 0 | 0 | 0 |
| 23 | 0 | 0 | 0 | 0 | 0 | 0 | 0 | 0 | 0 | 0 | 0 |

I claim:

1. A method of protecting wood comprising the steps of
   (a) treating said wood with a composition consisting essentially of 4,5-dichloro-2-n-octyl-3-isothiazolone and optionally, one or more compounds selected from the group consisting of propiconazole, tebuconazole, fenbuconazole, myclobutanil, azaconazole, iodopropargyl butyl carbamate, 2-thiocyanomethyl(thio)benzothiazole, chlorothalonil, permethrin, dichlofluanid, cyfluthrin, cypermethrin, s-fenvalerate, bifenthrin, o-phenylphenol, dithiocarbamate compounds, tributyltin oxide, pentachlorophenol, and quaternary compounds;
   a surfactant system consisting of at least one surfactant selected from the group consisting of sulfated anionics; sulfonated anionics; sulfosuccinated anionics; quaternary ammonium, cationics; and amphoterics; and
   at least one non-polar organic solvent selected from the group consisting of benzyl alcohol, benzyl acetate, pine oil, phenethyl alcohol, xylene, phenoxyethanol, butyl phthalate, 2,2,4-trimethyl-1,3-pentanediol, monoisobutyrate, mixtures of alkylbenzenes, P9 oil, long chain alkyl acrylate esters, and mineral spirits and
   (b) allowing said solvent to evaporate from said wood.

2. Method according to claim 1 wherein said wood is treated by applying said composition under pressure or under vacuum to said wood.

3. Method according to claim 1 wherein said surfactant system is selected from the group consisting of (a) sulfonated castor oil and dioctyl ester of sodium sulfosuccinic acid; and (b) amyl ester of sulfonated oleic acid, sodium salt and cocoamphocarboxypropionate.

4. Method according to claim 1 wherein said surfactant is a combination of surfactants selected from the group consisting of (a) two anionics; (b) an anionic and an amphoteric; (c) two quaternary ammonium cationics; (d) a quaternary ammonium cationic and an amphoteric; and (e) two quaternary ammonium cationics and an amphoteric.

* * * * *